United States Patent [19]
Conti et al.

[11] Patent Number: 5,057,149
[45] Date of Patent: Oct. 15, 1991

[54] METHOD AND APPARATUS FOR INTRODUCING UNIFORM QUANTITIES OF A MATERIAL INTO A METALLURGICAL SAMPLE

[75] Inventors: Richard F. Conti, Holland; Edwin Kaufman, Ambler, both of Pa.

[73] Assignee: ElectroNite International, N.V., Antwerp, Belgium

[21] Appl. No.: 461,493

[22] Filed: Jan. 5, 1990

[51] Int. Cl.⁵ .................................................. C21B 7/24
[52] U.S. Cl. ...................................... 75/377; 266/216; 266/79
[58] Field of Search .................... 266/79, 81, 44, 216; 75/376, 377; 73/DIG. 9

[56] References Cited

U.S. PATENT DOCUMENTS

| | | | |
|---|---|---|---|
| 3,452,602 | 6/1966 | Hackett | 73/DIG. 9 |
| 3,546,921 | 8/1967 | Bourke et al. | 73/DIG. 9 |
| 3,686,949 | 8/1972 | Hackett | 75/377 |
| 3,805,621 | 4/1974 | Falk | 73/DIG. 9 |
| 4,037,478 | 7/1977 | Cure | 73/DIG. 9 |
| 4,059,996 | 11/1977 | Cure | 73/DIG. 9 |
| 4,074,578 | 2/1978 | Collins | 73/425.4 R |
| 4,107,393 | 8/1978 | Frantzreb, Sr. et al. | 75/376 |
| 4,261,740 | 4/1981 | Plessers | 75/377 |
| 4,362,562 | 12/1982 | Plessers | 75/377 |
| 4,389,249 | 6/1983 | Holowaty et al. | 75/376 |
| 4,570,496 | 2/1986 | Falk | 75/377 |
| 4,667,715 | 5/1987 | Kaoepke et al. | 164/453 |

Primary Examiner—S. Kastler
Attorney, Agent, or Firm—Panitch Schwarze Jacobs & Nadel

[57] ABSTRACT

A method and apparatus for introducing an additive material into a metallurgical sample. In a preferred embodiment, the method and apparatus of the present invention comprises introducing a stabilizer, for example, tellurium and/or bismuth, into a metallurgical sample of cast iron or blast furnace hot metal to induce white solidification comprising a probe having a generally enclosed sample cavity and a conduit extending from the cavity for receiving a flow of molten metal for collection in the cavity. A distribution member proximate the conduit is employed for inserting a predetermined quantity of the additive material at a predetermined rate into the molten metal flowing through the conduit so that the additive material is homogeneously distributed throughout the molten metal within the sample cavity.

17 Claims, 1 Drawing Sheet

U.S. Patent     Oct. 15, 1991     5,057,149
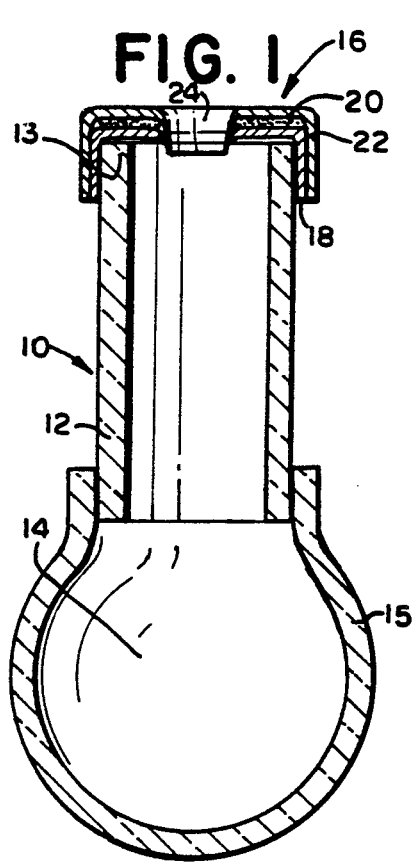
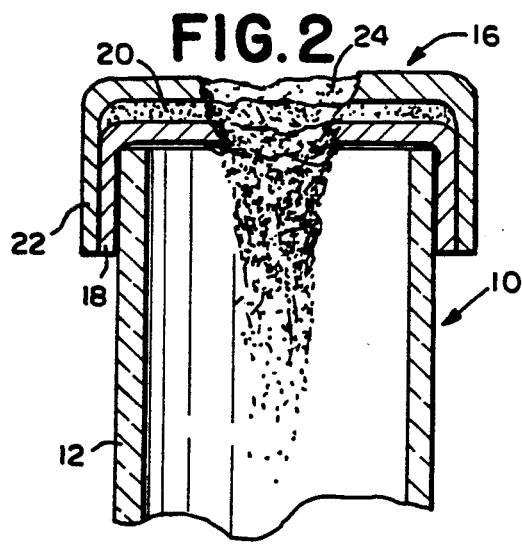
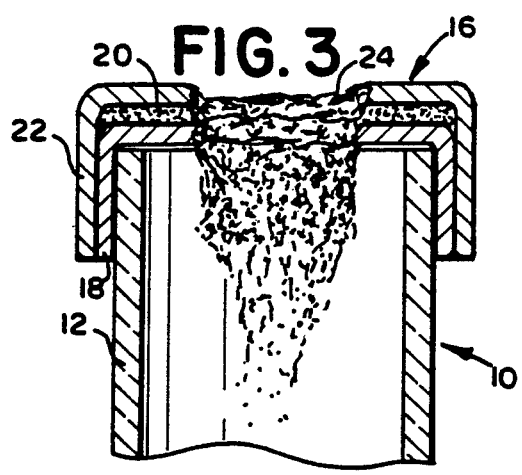
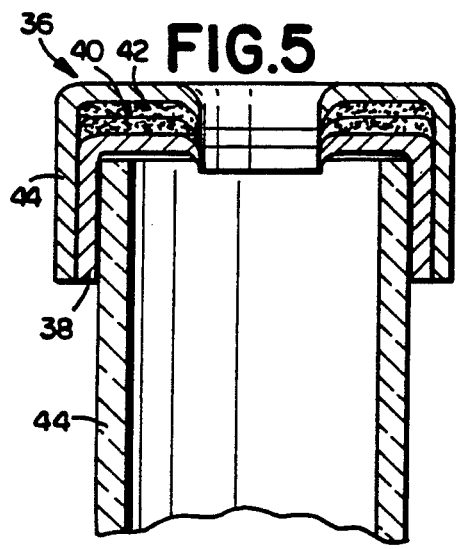
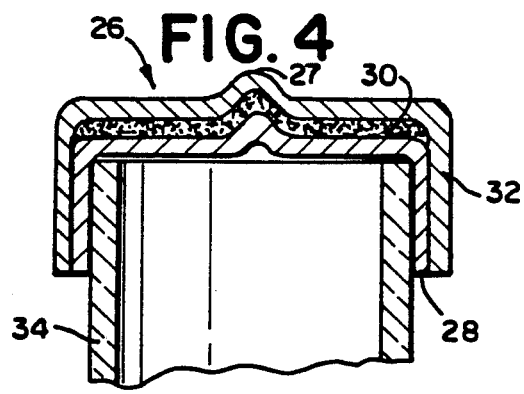

METHOD AND APPARATUS FOR INTRODUCING UNIFORM QUANTITIES OF A MATERIAL INTO A METALLURGICAL SAMPLE

BACKGROUND OF THE INVENTION

The present invention relates to a method and apparatus for introducing a material into a sample of molten metal. More specifically, the present invention relates to a method and apparatus for introducing a carbide stabilizer, such as tellurium and/or bismuth into a metallurgical sample of cast iron or blast furnace hot metal and for homogeneously distributing the stabilizer throughout the sample to induce white solidification.

During the processing of metal making, and in particular, during the molten processing of cast iron or blast furnace hot metal, it is often desirable to obtain samples of the metals for subsequent metallurgical analysis for ascertaining the precise chemical composition of the metal. With respect to certain grades of cast iron containing high concentrations of carbon and/or silicon and phosphorus, and especially blast furnace produced hot metal, the resulting solidified structure of a metallurgical sample will generally be in a form known in the industry as "gray iron". Gray iron refers to iron having enhanced graphite formation. Under certain circumstances, it is desirable for the metallurgical sample to have a "chilled" structure, also known in the industry as "white" iron. White iron refers to iron having enhanced carbide formation, and the process of forming white iron is called white solidification. A multitude of devices for collecting samples from a bath of molten metal have been proposed heretofore. A typical device comprises a molten metal sample cavity or chamber constructed from a suitable refractory material, such as foundry sand and cement. U.S. Pat. No. 3,452,602 discloses a typical collection device comprising a generally tubular conduit extending from the sampling cup or chamber, and is incorporated herein by reference. Upon insertion of the probe into a bath of molten metal, the molten metal is conveyed to the sampling cup or chamber via the conduit.

It is generally well known in the industry that a molten metal sample which would normally solidify as gray iron may be caused to solidify as white iron by using heavy cooling plates or particular sample cavity shapes of molten metal in the construction of the molten metal sampling chamber which promote white solidification. By using such cooling plates or cavity shapes, there is caused a generally rapid rate of solidification of the molten metal sample, promoting a white solidification structure. It is this rapid cooling process which gives rise to the term "chilled iron" when referring to white iron.

The problem associated with this type of approach is that the sample obtained may not be uniformly white throughout. I.e., within the same sample, there may be obtained a white or chilled surface layer, a mottled transition zone having both graphite and carbide structures and a gray iron interior. The depth of the white chilled surface layer may also vary, depending upon the particular metal composition and cast temperature, the structure and/or heat capacity of the chilling plates or the cavity structure. For example, graphite formation promoters within the molten metal and variations in the temperature of the molten metal at the time of sampling may cause variations in the amount of white chilled iron obtained. Each individual metallurgical sample must be separately prepared for analysis after solidification, for example, by the surface grinding of at least a portion of the sample for spectrometric or x-ray fluorescence analysis If the depth of the white chill layer in the sample is insufficient to provide a white chilled structure after the grinding and polishing steps, significant errors in the sample analysis may occur.

It is generally known in the art that various alloying elements may be used as stabilizing additives or stabilizers to enhance the tendency of gray iron to solidify as white iron. Such alloying elements have been used in sampling devices and sensors, such as phase detecting thermal analysis solidification cups, to promote white solidified iron. In addition, U.S. Pat. No. 3,546,921 discloses a method of producing the white chilled structure by introducing such a stabilizing additive for retarding primary graphite formation as the molten metal sample cools. This stabilizing additive is generally selected from one or more elements of bismuth, boron, cerium, lead, magnesium and tellurium.

There are a number of inherent problems associated with the existing methods employed for adding any of the aforementioned stabilizing additives to a molten metal sample for promoting white solidification. For example, it is generally necessary to insure that an adequate amount of the stabilizer is present in the molten metal sample to promote the formation of the white iron over a full range of sampling temperatures and chemistries, as mentioned in U.S. Pat. No. 4,059,996. If the temperature of the molten metal is too high, some or all of the stabilizer may burn or vaporize, resulting in a low efficiency of the additive and hence, only partial white solidification. If the molten metal sampling temperature is too low, the sample may solidify before becoming thoroughly mixed with the stabilizer, again resulting in only partial white solidification.

In addition, the stabilizer must be added in a manner providing generally uniform distribution of the stabilizer through the body of the sampling device. This uniform distribution is necessary to obtain a total white solidified cross section. Similar problems in the addition of deoxidants in molten steel sampling have been addressed in U.S. Pat. No. 4,037,478.

The present invention addresses the prior art problems of obtaining generally fully chill promoted white solidified molten metal samples and in homogeneously distributing a stabilizing additive throughout a molten metal sample by providing a mechanism for releasing a controlled amount of stabilizer into a sample of molten metal as it flows into the sample cavity without major modifications to any existing sampling device.

The present invention achieves the desired result by sandwiching the stabilizing additive between two layers of a melting material which melts at a known rate or by alloying or admixing the stabilizing additive with a melting material which melts at a known rate to provide a single layer device. The melting material may be a material having a high melting temperature, a low melting temperature or a temperature therebetween. Preferably, the melting material is a high melting temperature material, such as low carbon steel. Upon immersion of the sandwich device into a molten metal bath, the two layers admix or alloy with the molten metal at a controlled rate to expose the stabilizing additive to the molten metal flowing into the sample cavity. Upon immersion of the single layer device into a molten metal bath, the layer admixes or alloys with the molten metal at a controlled rate to alloy the stabilizing additive with the molten metal flowing into the sample cavity. The sandwich device and the single layer device are comprised of a cap member which is small enough to be located at the inlet or sampling chamber apparatus in the same manner as a protective inlet cap member which is currently used in prior art sampling devices.

SUMMARY OF THE INVENTION

Briefly stated, one aspect of the present invention relates to an apparatus and method for sampling molten metal comprising a probe having a generally enclosed sample cavity with an opening such that upon immersion of the probe into the molten metal a portion of the molten metal flows through the opening for collection within the sample cavity. Distribution means are provided proximate the opening for inserting a predetermined quantity of an additive material at a predetermined rate into the molten metal flowing into the sample cavity so that the additive material is homogeneously distributed throughout the molten metal within the sample cavity. In a preferred embodiment, the opening comprises a conduit extending from the sample cavity, the distribution means being proximate the conduit.

In another preferred embodiment, the distribution means comprises a cap member secured to the probe and covering at least a portion of the opening, the cap member comprising a first layer of material having a first predetermined melting temperature, the first layer of material having first and second surfaces, the first surface engaging the probe; a second layer formed of an additive material, the additive material layer having first and second surfaces, the first surface engaging the second surface of the first layer of material; and a third layer of material having a second predetermined melting temperature, the third layer of material having first and second surfaces, the first surface engaging the second surface of the additive material layer so that the additive material layer is generally enclosed between the first and third material layers, the first and second predetermined temperatures being selected so that the flow of molten metal through the opening admixes or alloys with the molten metal the first and third material layers at a predetermined rate to expose the additive material layer at a predetermined rate to the molten metal flowing through the opening whereby the additive material is alloyed into the molten metal flowing through the opening at a controlled rate to provide the homogeneous distribution of the additive material throughout the molten metal within the sample cavity. Furthermore, the opening preferably comprises a conduit extending from the sample cavity, the cap member covering at least a portion of the conduit.

BRIEF DESCRIPTION OF THE DRAWINGS

The foregoing summary, as well as the following detailed description, will be better understood when read in conjunction with the appended drawing. For the purpose of illustrating the invention, there is shown in the drawing embodiments which are presently preferred; it being understood, however, that this invention is not limited to the precise arrangements and instrumentality shown.

IN THE DRAWINGS

FIG. 1 is a sectional view of a portion of an apparatus for sampling molten metal in accordance with a presently preferred embodiment of the invention;

FIGS. 2 and 3 are sectional views of the apparatus of FIG. 1 demonstrating the sequential melting of the cap member by a flow of molten metal;

FIG. 4 is a sectional view of a portion of an apparatus for sampling molten metal in accordance with an alternate embodiment of the invention; and FIG. 5 is a sectional view of a portion of an apparatus for sampling molten metal in accordance with another alternate embodiment of the invention.

DETAILED DESCRIPTION OF THE PREFERRED EMBODIMENTS

Referring to the drawings, wherein like numerals refer to like elements throughout the several views, FIG. 1 illustrates a cross-sectional view of a portion of a first embodiment of an apparatus 10 for sampling molten metal.

The apparatus 10 represents a probe comprising a generally tubular conduit 12 extending from a generally enclosed sample cavity 14 which is defined by sample cavity shell 15 and is generally circular in cross-section in a manner well known in the art. The apparatus 10 provides a means of sampling and collecting molten metal from a molten metal bath for solidification and subsequent analysis also in a manner well known in the art. The apparatus 10 may be immersed into a bath of molten metal, thereby allowing a portion of the molten metal to flow through the conduit 12 and into the sample cavity 14. The size and shape of the conduit 12 and the sample cavity 14 and the material from which the conduit 12 and the sample cavity shell 15 are formed are well known in the art and therefore will not be discussed in detail herein since such information is not necessary for a complete understanding of the present invention.

A distribution means is installed on the probe, in the present embodiment proximate the conduit 12, as depicted in FIG. 1. The distribution means is employed for inserting a predetermined quantity of an additive material or stabilizer material, capable of alloying with molten metal, for example, an element, such as tellurium (Te), bismuth (Bi), boron (B), cerium (Ce), lead (Pb) or magnesium (Mg), at a predetermined rate into the molten metal flowing through the conduit 12 and into the sample cavity 14 so that the additive material is generally homogeneously distributed throughout the metal within the sample cavity 14. Preferably, the material comprises a stabilizer or stabilizing additive for promoting white chilled solidification of the molten metal sample. As previously discussed, an even or homogeneous distribution of the stabilizer results in the creation of a generally uniform or total white solidification cross section of the sample when solidified.

In the present or first preferred embodiment of the invention, the distribution means comprises a cap member 16 secured to the outer surface of the probe or to the conduit 12 (not shown) and covering at least a portion of the metal entrance end 13 of the conduit 12. The cap member is generally formed from a first material layer 18, a second additive material or stabilizer layer 20 and a third material layer 22.

The first layer of material 18 includes first and second surfaces, the first surface engaging the probe the entrance end of the conduit 12. The additive or stabilizer layer 20 includes first and second surfaces, the first surface engaging the second surface of the first layer of material 18. The third layer of material 22 also includes first and second surfaces, the first surface engaging the second surface of the stabilizer layer 20 and the second surface being generally exposed.

FIG. 1 illustrates that these three layers 18, 20 and 21 generally form a sandwich arrangement in which the stabilizer layer 20 is generally surrounded by or enclosed by the other two layers 18 and 22. In the present embodiment, the cap member 16 is generally circular in plan view to conform to the generally tubular shape of the conduit 12. However, as with the conduit 12 and the sample cavity 14, it is within the scope of the present invention to modify the size and shape of the cap member 10 sandwich arrangement to accommodate or conform to any size or geometry of the conduit 12 without departing from the scope of the present invention.

FIG. 1 further illustrates that the cap member 16 generally surrounds the entrance end of the conduit 12 so that molten metal flowing through the conduit 12 flows through a flow path formed of a generally circular aperture or opening 24 extending through the cap member 16 generally perpendicular to the first material layer 18, the second stabilizer layer 20 and the third material layer 22. The cap member 16 is preferably initially formed with the aperture 24 extending generally through its radial center with the dimension or diameter of the aperture 24 being smaller than the dimension or diameter of the conduit 12.

The first layer of material 18 preferably has a first predetermined melting temperature and the third layer of material 22 preferably has a second predetermined melting temperature. Preferably, the first layer 18 and the third layer 22 are formed of the same material and therefore the first predetermined melting temperature and the second predetermined melting temperature are generally the same.

In the present embodiment, the first and third material layers 18 and 22 comprise a high melting metallic material, such as low carbon steel. However, these layers could be formed of any other suitable metallic material, for example, aluminum or any other suitable nonmetallic material, for example, a polymeric material, having a desired melting temperature. In addition, the sandwich arrangement or single layer arrangement of the present invention may be used to introduce an element other than a stabilizing additive into the molten metal sample. In the sandwich arrangement, the first layer 18 and third layer 22 may comprise a material, for example, aluminum, having a lower melting temperature than the melting temperature of low carbon steel.

Alternatively, the first layer 18 may comprise a material, for example, aluminum, and the third layer 22 may comprise a different material, for example, low carbon steel or a polymeric material. This arrangement may be used, for example, for alloying aluminum, in the form of first layer 18, into the molten metal sample. In this manner, the quantity of aluminum to be alloyed into the molten metal sample may be adjusted by varying the thickness of the first layer 18.

When the first and third material layers 18 and 22 comprise a high melting metallic material, such as low carbon steel, the rate of melting and alloying of the first material layer 18 and the third material layer 22 with the molten metal is dependent upon the rate of carbon diffusion from the molten metal to the layers 18 and 22, since low carbon steel has a higher melting temperature than iron, thereby lowering the melting temperature of the cap member 16 to that of the molten metal bath. The first predetermined melting temperature and the second predetermined melting temperature may be higher or lower than the melting temperature of the molten metal to be sampled.

When the first and third material layers 18 and 22 comprise a nonmetallic melting material, such as a polymeric material, the first material layer 18 and the third material layer 22 melt and admix with the molten metal when the first and third material layers contact the molten metal. The first predetermined melting temperature and the second predetermined melting temperature may be higher or lower than the melting temperature of the molten metal to be sampled. However, in the case of a polymeric material, the first and second predetermined melting temperatures are generally lower than the temperature of the molten metal to be sampled.

Preferably, the first predetermined melting temperature and the second predetermined melting temperature are slightly higher than the temperature of the molten metal to be sampled. In this manner, when the probe is inserted into the molten metal, the molten metal flowing through the aperture 24 and the conduit 12 causes portions of the first material layer 18 and the third material layer 22 proximate the aperture 24 to melt and alloy and/or admix with the molten metal at a controlled rate to thereby expose the stabilizer layer 22 to the molten metal flowing through the aperture 24 and the conduit 12 for collection within the sample cavity 14.

The stabilizer layer 20 is comprised of a substance which promotes carbide formation in molten metal. In the preferred embodiment, the stabilizer layer 20 comprises tellurium (Te). Alternatively, the stabilizer layer 20 could comprise bismuth (Bi), a combination of tellurium and bismuth, or any other known stabilizer element or any combination of such elements.

The amount of the stabilizer to be added to the molten metal in the sample cavity is an amount effective to promote carbide formation in the molten metal sample.

Preferably, the amount of the stabilizer to be added to a sample of molten metal in the sample cavity 14 is about 0.100% by weight. However, one skilled in the art would recognize that the amount of the stabilizer to be added to the molten metal sample to promote carbide formation in the molten metal sample is variable and is a function of the molten metal sampling temperature, the stabilizer added to the molten metal and, in general, the iron chemistry of the molten metal sample. Hence, the amount of the stabilizer to be added to the molten metal sample may be greater than or less than 0.100% by weight. For example, a stabilizer of at least 0.02% by weight has been shown to be effective. One skilled in the art would also recognize that an alloy of tellurium and/or bismuth could be used such that the amount of the stabilizing tellurium and/or bismuth added to the molten metal sample is generally around 0.100% by weight. For example, an iron/tellurium alloy (50% by weight iron/50% by weight tellurium), having a total weight of about 2 g may be added to about a 100 g sample of molten metal. In this manner, about 0.1 g of tellurium has been added to about 100 g of molten metal, thereby obtaining the preferred 0.100% by weight of stabilizer. Alternatively, a stabilizer layer 20 comprising a bismuth/lead alloy which is ductile enough to provide a thin preformed wafer to be sandwiched between the first material layer 18 and the third material layer 22 may be used.

Subsequent analysis of samples obtained by the above method have indicated an efficiency of addition to be approximately 80%. One skilled in the art would recognize that recovery of the alloy, directly proportional to the efficiency of addition, is that part of the addition which effects stabilization. The amount of desired alloy recovery to effect total white solidification is a function of other factors described earlier, such as metal composition, sampling temperature, etc. Having a method for controlled release of an alloy at a repeatable efficiency allows the tailoring of the sample device in terms of stabilizer added to match the conditions of sampling.

In addition, the tellurium and bismuth and their respective alloys may be in a granular or powdered form. Preferably, the tellurium and bismuth and their respective alloys are in powdered form, facilitating the alloying and even distribution of the tellurium and bismuth throughout the molten metal sample.

FIGS. 2 and 3 together illustrate the method of operation of the embodiment of the present invention shown in FIG. 1.

Molten metal is collected by immersing apparatus 10 into a molten metal bath (not shown). FIG. 2 illustrates the cap member 16 after molten metal has just begun to flow through the aperture 24 and the conduit 12. The flow of the molten metal through the conduit 12 via the aperture 24 admixes and/or alloys with the molten metal the portion of the first material layer 18 and the third material layer 22 proximate the aperture 24 at a predetermined rate to expose the stabilizer layer 20 at a predetermined rate to the molten metal flowing through the conduit 12. In this manner, the stabilizer layer 20 is alloyed with the molten metal flowing through the conduit 12 at a predetermined rate related to the molten metal flow rate to provide a homogeneous distribution of the stabilizer material throughout the molten metal within the sample cavity 14. FIG. 3 illustrates the cap member 16 after additional molten metal has flowed through the conduit 12 after the time illustrated in FIG. 2. As FIG. 2 and FIG. 3 illustrate, the cross-sectional dimension of the aperture 24 in the cap member 16 while being initially smaller than the cross-sectional dimension of the conduit 12, increases in dimension as the molten metal flows through the conduit 12.

FIG. 4 illustrates an alternate embodiment of the distribution means which provides the desired timed release of the molten metal stabilizing material. As in the aforementioned preferred embodiment, the distribution means preferably comprises a cap member 26 comprised of the same three layers. The first material layer 28 and the third material layer 32 are generally parallel to each other and form a raised bump 27 generally in the center of the cap member 26. FIG. 4 further illustrates that the first material layer, 28, the second stabilizer layer 30 and the third material layer 32 are contiguous throughout the non-raised portion and generally provide a cap member 26 that initially completely covers the conduit 34, prior to immersing apparatus into the molten metal bath. The raised bump 27 functions as an initial starting location for the melting and alloying and/or admixing with the molten metal of the cap member 26 by the molten metal. The melting of the raised bump 27 results in the creation of an aperture (not shown) through the cap member 26 and provides the same results as discussed above with respect to the embodiment of FIG. 1.

FIG. 5 illustrates another alternate embodiment of the present invention. In FIG. 5, as in the previous embodiments, the distribution means comprises a cap member 36. Also as in the previous embodiments, FIG. 5 illustrates that the cap member comprises several layers, generally forming a sandwich arrangement. However, in the arrangement of FIG. 5, the cap member 36 comprises two generally parallel layers 40 and 42 of material to be introduced into the molten metal sample. The layers 40 and 42 may be of the same material or may each be a different material. For example, the layer 40 may comprise tellurium and the layer 42 may comprise bismuth. Alternatively, the layers 10 and 42 may comprise an alloy of tellurium or bismuth or any other such elements, as set forth above.

Moreover, if one of the two layers 40 and 42, for example, the layer 40 is a stabilizing additive, for example, tellurium, the other layer, for example, the layer 42 may comprise a material other than tellurium or bismuth, for example, aluminum. Aluminum is both a deoxidant and a graphite promoter as opposed to a carbide stabilizer which promotes a white chilled structure of the molten metal sample. Adding a deoxidant to a sample of molten metal, such as aluminum, generally results in a metal sample having, after solidification, a lower sample porosity. Such a lower porosity sample is generally easier to grind and polish when preparing the sample for analysis.

If, for example, the layer 42 comprises aluminum, the amount of the layer 40 stabilizing additive, for example, tellurium, to be added to the molten metal sample is necessarily increased. This increased amount of tellurium to be added to the molten metal sample compensates for the reduced chilling effect of aluminum on the molten metal sample.

Although not illustrated, an alternate embodiment of the distribution means of the present invention may comprise a single layer device as opposed to the aforementioned sandwich devices. This single layer device also provides the desired timed release of the molten metal stabilizing material. In this embodiment, the distribution means preferably comprises a cap member comprised of a single layer. This layer may be an alloy of a high melting metallic material, for example, low carbon steel and a stabilizing additive material, for example, tellurium. Alternatively, the single layer may comprise an alloy of any other suitable melting metallic material, for example, aluminum, and a stabilizing additive material. Additionally, the single layer may comprise an admixture of a nonmetallic material, for example, a polymeric material and a stabilizing additive material. The melting and alloying and/or admixing of the single layer cap member with the molten metal is then performed in a fashion similar to the aforementioned preferred embodiments.

From the foregoing description and the appended drawing, it can be seen that the present invention comprises an apparatus and method for homogeneously distributing an additive material, such as a stabilizer through a metal sample within a sample cavity. It will be recognized by those skilled in the art that the above-described embodiments are merely illustrative of one form of the invention and that the invention may be embodied in other specific forms without departing from the spirit or essential attributes thereof. Therefore, reference should be made to the appended claims, rather than to the foregoing specification as indicating the scope and spirit of the invention.

We claim:

1. In an apparatus for sampling molten metal comprising a probe having a generally enclosed sample cavity with an opening such that upon immersion of the probe into the molten metal a portion of the molten metal flows through the opening for collection within the sample cavity, wherein the improvement comprises distribution means proximate the opening for inserting a predetermined quantity of additive material into the molten metal which flows through the opening, the distribution means comprising:

a first layer of material having a first predetermined melting temperature, the first layer of material having first and second surfaces, the first surface engaging the probe proximate the opening;

a second layer formed of an additive material, the additive material layer having first and second surfaces, the first surface of the second layer engaging the second surface of the first layer of material; and a third layer of material having a second predetermined melting temperature, the third layer of material having first and second surfaces, the first surface of the third layer of material engaging the second surface of the additive material layer so that the additive material layer is generally sandwiched between the first and third material layers, the materials of the first and third layer being selected so that the first and third material layers melt at a controlled rate as the molten metal flows through the opening to expose the additive material to the molten metal at said controlled rate whereby the additive material is alloyed into the molten metal flowing through the opening at a controlled rate so that the additive material is generally homogeneously distributed throughout the molten metal entering the sample cavity.

2. The apparatus according to claim 1 wherein the opening comprises a conduit extending from the sample cavity, the distribution means being proximate the conduit.

3. The apparatus according to claim 1 wherein the second layer comprises a carbide stabilizer.

4. The apparatus according to claim 1 wherein the first and second predetermined melting temperatures are the same.

5. The apparatus according to claim 1 wherein the distribution means generally surrounds the opening so that molten metal flowing through the opening flows generally perpendicular to the first, second and third layers.

6. The apparatus according to claim 1 wherein the distribution means generally surrounds the conduit so that molten metal flowing through the conduit flows generally perpendicular to the first, second and third layers.

7. The apparatus according to claim 6 wherein a flow path extends through the distribution means and communicates with the conduit for the flow of molten metal through the conduit, the cross-sectional dimension of the distribution means flow path being initially smaller than the cross-sectional dimension of the conduit, the distribution means flow path cross section increasing as the molten metal flows through the conduit and the layers are admixed or alloyed with the molten metal.

8. The apparatus according to claim 1 wherein the distribution means generally surrounds and covers an entrance end of the conduit, wherein the first layer, second layer and third layer are generally parallel to each other and form a raised bump generally in the center of the cap member.

9. The apparatus according to claim 1 wherein the first layer and the third layer comprise a low carbon steel.

10. The apparatus according to claim 1 wherein the second layer is comprised of a substance which promotes carbide formation in molten metal.

11. The apparatus according to claim 1 wherein the second layer comprises tellurium.

12. The apparatus according to claim 1 wherein the second layer comprises bismuth.

13. The apparatus according to claim 1 wherein the additive comprises tellurium and bismuth.

14. A method for introducing an additive material into a molten metal sample comprising:

(a) providing a probe having a generally enclosed sample cavity with an opening for directing molten metal into the sample cavity;

(b) providing a distribution means proximate the opening for inserting a predetermined quantity of additive material into the molten metal flowing through the opening and into the sample cavity, the distribution means comprising:

(i) a first layer of material having a first predetermined melting temperature, the first layer of material having first and second surfaces, the first surface of the first layer of material engaging the probe proximate the opening, (ii) a second layer formed of an additive material, the additive material layer having first and second surfaces, the first surface of the additive material engaging the second surface of the first layer of material, and (iii) a third layer of material having a second predetermined melting temperature, the third layer of material having first and second surfaces, the first surface of the third layer of material engaging the second surface of the additive material layer so that the additive material layer is generally sandwiched between the first and third material layers, the material of the first and third layer being selected so that the first and third material layers melt at a controlled rate as molten metal flows through the opening to expose the additive material to molten metal at the controlled rate; and (c) immersing the probe into molten metal so that a portion of the molten metal flows through the opening and receives the additive material at the controlled rate whereby the additive material is alloyed into the molten metal flowing through the opening at the controlled rate so the additive material is generally homogeneously distributed throughout the molten metal entering the sample cavity.

15. The method of claim 14 wherein the opening comprises a conduit extending from the sample cavity, the distribution means being proximate the conduit.

16. The method of claim 14 wherein the additive material comprises a carbide stabilizer.

17. The method of claim 14 wherein the opening comprises a conduit extending from the sample cavity, the distribution means covering at least a portion of the conduit.

* * * * *